US012758728B2

(12) United States Patent
Dong et al.

(10) Patent No.: US 12,758,728 B2
(45) Date of Patent: Oct. 13, 2026

(54) METHOD AND SYSTEM FOR ADDRESSING HYPERVENTILATION BASED ON VENTILATOR DEVICE

(71) Applicant: GUANGZHOU LANSWICK MEDICAL TECHNOLOGY CO., LTD., Guangzhou (CN)

(72) Inventors: Hui Dong, Guangzhou (CN); Longchao Zhao, Guangzhou (CN); Caixin Sun, Guangzhou (CN)

( * ) Notice: Subject to any disclaimer, the term of this patent is extended or adjusted under 35 U.S.C. 154(b) by 666 days.

(21) Appl. No.: 18/266,590

(22) PCT Filed: Mar. 24, 2023

(86) PCT No.: PCT/CN2023/083666
§ 371 (c)(1),
(2) Date: Jun. 12, 2023

(87) PCT Pub. No.: WO2023/213154
PCT Pub. Date: Nov. 9, 2023

(65) Prior Publication Data

US 2024/0382705 A1 Nov. 21, 2024

(30) Foreign Application Priority Data

May 5, 2022 (CN) ........................ 202210480186.X

(51) Int. Cl.
*A61M 16/00* (2006.01)
*A61B 5/145* (2006.01)
(Continued)

(52) U.S. Cl.
CPC ....... *A61M 16/024* (2017.08); *A61B 5/14539* (2013.01); *A61B 5/14542* (2013.01);
(Continued)

(58) Field of Classification Search
CPC .. A61M 16/024; A61M 16/12; A61M 16/026; A61M 16/022; A61M 2016/103;
(Continued)

(56) References Cited

U.S. PATENT DOCUMENTS 5,320,093 A * 6/1994 Raemer ............... A61M 16/085 128/914
2004/0144383 A1* 7/2004 Thomas .............. A61M 16/085 128/204.18

(Continued)

*Primary Examiner* — Brandy S Lee
*Assistant Examiner* — Sara K Toich

(57) ABSTRACT

A method and a system for addressing hyperventilation based on a ventilator device execute steps of: obtaining a carbon dioxide partial pressure of a subject, and determining whether the subject has respiratory alkalosis based on the carbon dioxide partial pressure; obtaining vital sign data of the subject when the respiratory alkalosis occurs and determining a degree of the respiratory alkalosis based on the vital sign data; and adjusting a mixing ratio of oxygen and carbon dioxide based on the degree of the respiratory alkalosis, then re-supplying the subject, and monitoring a respiratory status in real time. The system can quickly and accurately determine whether a subject has respiratory alkalosis by monitoring the carbon dioxide partial pressure, and can effectively alleviate respiratory alkalosis by adjusting mixing ratio of oxygen and carbon dioxide, thus improving the efficiency and safety of resolving respiratory alkalosis caused by hyperventilation.

1 Claim, 2 Drawing Sheets

(51) Int. Cl.
*A61M 16/10* (2006.01)
*A61M 16/12* (2006.01)

(52) U.S. Cl.
CPC .... *A61M 16/0066* (2013.01); *A61M 16/1005* (2014.02); *A61M 16/12* (2013.01); *A61M 2202/0007* (2013.01); *A61M 2202/0208* (2013.01); *A61M 2202/0225* (2013.01); *A61M 2205/3303* (2013.01); *A61M 2205/3327* (2013.01); *A61M 2205/3331* (2013.01); *A61M 2205/50* (2013.01); *A61M 2230/005* (2013.01); *A61M 2230/208* (2013.01); *A61M 2230/432* (2013.01)

(58) Field of Classification Search
CPC ...... A61M 2230/202; A61M 2230/208; A61M 2230/005; A61M 2202/0225; A61M 2205/3324; A61B 5/145; A61B 5/14539; A61B 5/14542; A61B 5/7221
See application file for complete search history.

(56) References Cited

U.S. PATENT DOCUMENTS

| | | | | | |
|---|---|---|---|---|---|
| 2007/0169779 | A1* | 7/2007 | Freeman | A61M 16/12 128/204.22 |
| 2007/0240718 | A1* | 10/2007 | Daly | A61M 16/08 128/204.22 |
| 2016/0296159 | A1* | 10/2016 | Larson | G16H 20/00 |
| 2021/0330996 | A1* | 10/2021 | Studer | A62B 7/00 |
| 2021/0369995 | A1* | 12/2021 | Kuzelka | G01N 33/0031 |
| 2022/0238216 | A1* | 7/2022 | Shelton, IV | G16H 40/40 |

* cited by examiner

METHOD AND SYSTEM FOR ADDRESSING HYPERVENTILATION BASED ON VENTILATOR DEVICE

BACKGROUND OF THE PRESENT INVENTION

Field of Invention

The present invention relates to a technical field of ventilators, and more particularly to a method and a system for addressing hyperventilation based on a ventilator device.

Description of Related Arts

Currently, ventilators are a commonly accepted device for emergency and treatment of respiratory diseases, and are widely used in hospitals for emergency, intensive care, and bedside respiratory resuscitation and treatment in various departments. Current composition of ventilation is oxygen $O_2$ and air, which are mixed in different proportions according to the patient's condition, and then supplied to the patient to meet the patient's demand for oxygen.

However, when respiratory resuscitation and treatment are carried out by ventilator, it is easy to cause hyperventilation for the patient, which leads to respiratory alkalosis and puts the patient at a certain risk. Conventional ventilator cannot quickly detoxify the patient in case of respiratory alkalosis, and the relief efficiency and effect are insufficient.

Therefore, the present invention provides a method and a system for addressing hyperventilation based on a ventilator device, which can quickly and accurately determine whether a subject has respiratory alkalosis by monitoring the carbon dioxide partial pressure of the subject, and can effectively alleviate respiratory alkalosis of the subject by adjusting the mixing ratio of oxygen and carbon dioxide, thus improving the efficiency and safety of resolving respiratory alkalosis caused by hyperventilation.

SUMMARY OF THE PRESENT INVENTION

An object of the present invention is to provide a method and a system for addressing hyperventilation based on a ventilator device, which can quickly and accurately determine whether a subject has respiratory alkalosis by monitoring the carbon dioxide partial pressure of the subject, and can effectively alleviate respiratory alkalosis of the subject by adjusting the mixing ratio of oxygen and carbon dioxide, thus improving the efficiency and safety of resolving respiratory alkalosis caused by hyperventilation.

The present invention provides a method for addressing hyperventilation based on a ventilator device, comprising steps of:

- step 1: obtaining a carbon dioxide partial pressure of a subject, and determining whether the subject is experiencing respiratory alkalosis based on the carbon dioxide partial pressure;
- step 2: obtaining vital sign data of the subject when the respiratory alkalosis occurs and determining a degree of the respiratory alkalosis of the subject based on the vital sign data; and
- step 3: adjusting a mixing ratio of oxygen and carbon dioxide based on the degree of the respiratory alkalosis, then re-supplying the subject, and monitoring a respiratory status of the subject in real time.

Preferably, according to the step 1 of the method, obtaining the carbon dioxide partial pressure of the subject comprises steps of:

- obtaining a ventilation start moment of the subject, and generating target control instructions based on the ventilation start moment;
- controlling a predetermined sensor based on the target control instructions, and moving a detection probe of the predetermined sensor to a target detection site of the subject based on the target control instructions; and
- obtaining the carbon dioxide partial pressure of the subject via the detection probe based on the target detection site, and displaying the carbon dioxide partial pressure in real time on a predetermined displayer.

Preferably, according to the method, displaying the carbon dioxide partial pressure in real time on the predetermined displayer comprises steps of:

- obtaining the carbon dioxide partial pressure of the subject, and ranking the carbon dioxide partial pressure of the subject;
- determining target values of the carbon dioxide partial pressure at different time points based on a ranking result, and preprocessing the carbon dioxide partial pressure based on the target values to obtain effective carbon dioxide partial pressure;
- extracting data characteristics of the carbon dioxide partial pressure, and determining waveform amplitudes and target points based on the data characteristics;
- calling a predetermined visualization component based on the waveform amplitude and the target points, and convert a format of the effective carbon dioxide partial pressure based on the visualization component, so as to obtain graphical data to be displayed; and
- labeling the graphical data to be displayed in a target graph to obtain a waveform graph of the carbon dioxide partial pressure of the subject, and displaying the waveform graph in real time on the predetermined displayer.

Preferably, according to the step 1 of the method, determining whether the subject is experiencing respiratory alkalosis based on the carbon dioxide partial pressure comprises steps of:

- obtaining the carbon dioxide partial pressure of the subject, meanwhile obtaining historical training data; determining a standard fluctuation range of the carbon dioxide partial pressure based on the historical training data;
- comparing the carbon dioxide partial pressure of the subject with the standard fluctuation range;
- if the carbon dioxide partial pressure of the subject is not within the standard fluctuation range, determining whether the carbon dioxide partial pressure of the subject is less than a minimum value of the standard fluctuation range, and if it is less than the minimum value of the standard fluctuation range, determining that the subject satisfies respiratory alkalosis characteristics and providing an alarm alert; and
- otherwise, determining the carbon dioxide partial pressure of the subject to be normal, and continuously monitoring the carbon dioxide partial pressure of the subject.

Preferably, according to the method, determining that the subject satisfies the respiratory alkalosis characteristics comprises steps of:

- collecting a blood sample from the subject based on a predetermined sampling device and performing a PH analysis on the blood sample to obtain a PH value of the subject;

determining acidity or alkalinity of the subject based on the PH value, and determining that the subject has respiratory alkalosis when the subject is alkaline; and otherwise, determining that the subject has an abnormal carbon dioxide partial pressure, and determining a target cause of the abnormal carbon dioxide partial pressure, and optimizing the ventilator device based on the target cause.

Preferably, according to the step 2 of the method, obtaining the vital sign data of the subject when the respiratory alkalosis occurs and determining the degree of the respiratory alkalosis of the subject based on the vital sign data comprise steps of obtaining ID information of a predetermined vital sign measuring device and receiving a vital sign data package collected by the predetermined vital sign measuring device based on the ID information, wherein the predetermined sign measuring device comprises at least one device type;

determining the device type of the predetermined vital sign measuring device based on the ID information, and determining a correspondence between the predetermined vital sign measuring device and a predetermined protocol plug-in based on the device type;

determining a target protocol plug-in for the predetermined vital sign measuring device based on the correspondence, and performing protocol parsing of the vital sign data package based on the target protocol plug-in to obtain initial vital sign data;

extracting attribute information of the initial vital sign data, and determining target cleaning rules for data cleaning of the initial vital sign data based on the attribute information;

cleaning the initial vital sign data based on the target cleaning rules, thereby obtaining target vital sign data of the subject; classifying the target vital sign data based on the attribute information, so as to obtain a target classification result;

determining a waveform profile corresponding to each type of the target vital sign data based on the target classification result, and setting a reference peak point in the waveform profile;

traversing forwards and backwards based on the reference peak points and removing ghost peaks from the waveform profile based on traversal results, so as to obtain a peak time series corresponding to each type of the target vital sign data;

calculating an average spacing of adjacent peak points based on the peak time series, and determining a target change value corresponding to each type of the target vital sign data of the subject based on the average spacing;

performing differentiating calculation on the target change value and a corresponding predetermined threshold to obtain a corresponding target difference value, and comparing the target difference value with the standard fluctuation range corresponding to each type of the target vital sign data; and determining a pH status of the subject based on a comparison result, and determining the degree of the respiratory alkalosis of the subject based on the pH status.

Preferably, according to the method, determining a pH status of the subject based on a comparison result, and determining the degree of the respiratory alkalosis of the subject based on the pH status comprises steps of:

obtaining the pH status of the subject, and determining bicarbonate ion concentration in the subject based on the pH status;

determining a concentration difference between the bicarbonate ion concentration and a standard bicarbonate ion concentration threshold, and comparing the concentration difference with a first difference threshold and a second difference threshold, respectively;

if the concentration difference is less than the first difference threshold, determining that the subject has mild respiratory alkalosis and sending a first alarm alert; and if the concentration difference is no less than the first difference threshold and less than the second difference threshold, determining that the subject has moderate respiratory alkalosis and sending a second alarm alert; and otherwise, determining that the subject has severe respiratory alkalosis and sending a third alarm alert.

Preferably, according to the step 3 of the method, adjusting the mixing ratio of the oxygen and the carbon dioxide based on the degree of the respiratory alkalosis, then re-supplying the subject, and monitoring the respiratory status of the subject in real time comprise steps of:

obtaining the degree of the respiratory alkalosis of the subject, meanwhile sampling a gas mixture currently received by the subject and analyzing the gas mixture based on a sampling result, so as to obtain an initial mixing ratio of the oxygen and the carbon dioxide in the gas mixture;

extracting a target characteristic of the degree of the respiratory alkalosis in the subject and determining a target carbon dioxide ratio adjustment range for mitigating the degree of the respiratory alkalosis in the subject based on the target characteristic, wherein the target carbon dioxide ratio adjustment range is 1%-6%;

determining an initial adjustment parameter for a carbon dioxide mixing ratio in the initial mixing ratio of the oxygen and the carbon dioxide based on the target carbon dioxide ratio adjustment range, and adjusting the initial mixing ratio of the oxygen and the carbon dioxide based on the initial adjustment parameter to obtain a baseline mixing ratio;

determining a gas pressure of the oxygen and the carbon dioxide through the ventilator device based on the baseline mixing ratio, and regulating a pressure balance of the oxygen and the carbon dioxide based on the gas pressure;

mixing the oxygen with the carbon dioxide based on a pressure balance regulation result to obtain a baseline gas mixture, and delivering the baseline gas mixture to the subject based on the ventilator device;

monitoring respiration data of the subject in real time based on a delivery result, and adjusting a carbon dioxide ratio in the baseline gas mixture in a gradient form based on the respiration data; and determining a delivering period of the gas mixture of each gradient based on gradient adjustment results, and delivering the gas mixture of each gradient to the subject based on the delivering period until the respiratory data of the subject returns to normal, thus completing mixture adjustment of the oxygen and the carbon dioxide.

Preferably, according to the method, monitoring respiration data of the subject in real time based on the delivery result comprises steps of:

obtaining a real-time monitoring result of the respiratory data of the subject, and determining a heartbeat waveform profile corresponding to the respiratory data of the subject based on the real-time monitoring result;

determining whether the subject has respiratory abnormalities based on the heartbeat waveform profile;

determining a target cause of the respiratory abnormalities of the subject if the respiratory abnormalities exist, and adjusting the respiratory abnormalities of the subject based on the target cause; and otherwise, monitoring the respiratory data of the subject in real time until the respiratory data of the subject returns to normal, then switching an operating mode of the ventilator device, wherein the operating mode comprises mixing oxygen and carbon dioxide and mixing oxygen and air.

Preferably, a system for addressing hyperventilation based on a ventilator device is provided, comprising:

a monitoring module for obtaining a carbon dioxide partial pressure of a subject, and determining whether the subject is experiencing respiratory alkalosis based on the carbon dioxide partial pressure;

an analyzing module for obtaining vital sign data of the subject when the respiratory alkalosis occurs and determining a degree of the respiratory alkalosis of the subject based on the vital sign data; and an adjusting module for adjusting a mixing ratio of oxygen and carbon dioxide based on the degree of the respiratory alkalosis, then re-supplying the subject; and monitoring a respiratory status of the subject in real time.

Other features and advantages of the present invention will be set forth in the following description, and will partially become apparent from the specification or from the implementation of the present invention. The objects and other advantages of the present invention may be achieved and obtained through the structure as specifically indicated in the written specification, the claims, and the accompanying drawings.

The technical solutions of the present invention will be further described below with the accompanying drawings and embodiments.

BRIEF DESCRIPTION OF THE DRAWINGS

The accompanying drawings are intended to provide a further understanding of the present invention and form part of the specification, which will be used in conjunction with the embodiments of the present invention to be exemplary only instead of being limiting. In the accompanying drawings.

DETAILED DESCRIPTION OF THE PREFERRED EMBODIMENT

The embodiments of the present invention will be described below in conjunction with the accompanying drawings. It is to be understood that the embodiments described herein are exemplary only and are not intended to be limiting.

Embodiment 1

Figure 1:
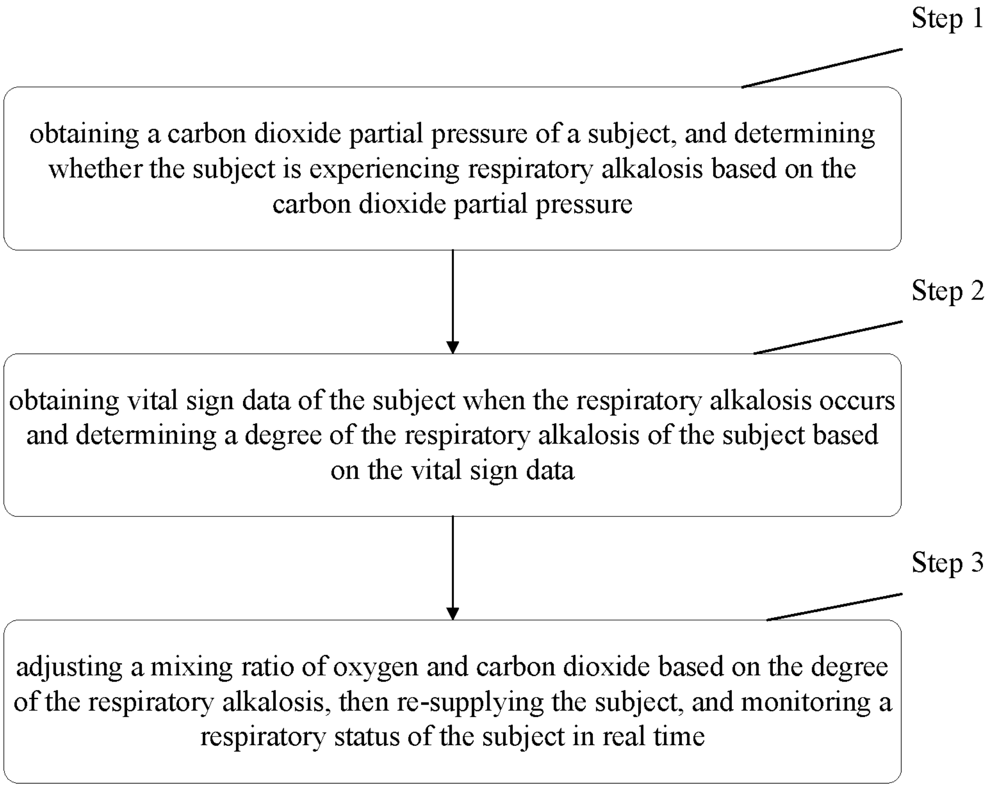
FIG. 1 is a flow chart of a method for addressing hyperventilation based on a ventilator device according to an embodiment of the present invention.

This embodiment provides a method for addressing hyperventilation based on a ventilator device, as shown in FIG. 1, comprising steps of:

step 1: obtaining a carbon dioxide partial pressure of a subject, and determining whether the subject is experiencing respiratory alkalosis based on the carbon dioxide partial pressure;

step 2: obtaining vital sign data of the subject when the respiratory alkalosis occurs and determining a degree of the respiratory alkalosis of the subject based on the vital sign data; and step 3: adjusting a mixing ratio of oxygen and carbon dioxide based on the degree of the respiratory alkalosis, then re-supplying the subject, and monitoring a respiratory status of the subject in real time.

In this embodiment, the subject refers to a patient or casualty who is being supplied via a ventilator.

In this embodiment, the carbon dioxide partial pressure refers to arterial carbon dioxide and end-expiratory carbon dioxide, wherein the arterial carbon dioxide is used to reflect a carbon dioxide level in patient's arterial blood, and end-expiratory carbon dioxide is used to reflect patient's pulmonary ventilation.

In this embodiment, determining whether the subject is experiencing respiratory alkalosis based on the carbon dioxide partial pressure means that the subject is determined to have respiratory alkalosis when the carbon dioxide partial pressure of the subject is below a normal range.

In this embodiment, the vital sign data refers to subject heart rate, blood pressure, pulse beat rate, etc.

In this embodiment, the degree of the respiratory alkalosis refers to an extent to which the subject body PH is significantly high due to the hyperventilation during treatment with the ventilator device.

In this embodiment, adjusting the mixing ratio of the oxygen and the carbon dioxide based on the degree of the respiratory alkalosis means that the carbon dioxide ratio is appropriately increased to alleviate the respiratory alkalosis of the subject.

In this embodiment, monitoring the respiratory status of the subject in real time refers to real-time monitoring of changes in subject physical parameters after air supply regimen is changed, wherein the mixing ratio of the oxygen and the carbon dioxide is dynamically adjusted based on the relief of the respiratory alkalosis in the subject.

The beneficial effect of the above technical solution is that the method can quickly and accurately determine whether a subject has respiratory alkalosis by monitoring the carbon dioxide partial pressure of the subject, and can effectively alleviate respiratory alkalosis of the subject by adjusting the mixing ratio of oxygen and carbon dioxide, thus improving the efficiency and safety of resolving respiratory alkalosis caused by hyperventilation.

Embodiment 2

Based on the embodiment 1, according to the step 1 of the method, obtaining the carbon dioxide partial pressure of the subject comprises steps of:

obtaining a ventilation start moment of the subject, and generating target control instructions based on the ventilation start moment;

controlling a predetermined sensor based on the target control instructions, and moving a detection probe of the predetermined sensor to a target detection site of the subject based on the target control instructions; and obtaining the carbon dioxide partial pressure of the subject via the detection probe based on the target detection site, and displaying the carbon dioxide partial pressure in real time on a predetermined displayer.

In this embodiment, the ventilation start moment refers to time information when the subject receives gas from the ventilator device.

In this embodiment, the target control instruction refers to controlling a machine to detect the carbon dioxide partial pressure, so as to facilitate the acquisition of the carbon dioxide partial pressure of the subject.

In this embodiment, the predetermined sensor is set up in advance to monitor the carbon dioxide partial pressure in the subject, which is, for example, a blood gas analyzer.

In this embodiment, the target detection site refers to a certain part of the body, such as arm, where the carbon dioxide partial pressure of the subject is measured.

In this embodiment, the predetermined displayer is preprogrammed on the predetermined sensor to display the real-time monitored carbon dioxide partial pressure.

The beneficial effect of the above technical solution is that by determining the ventilation start moment, the carbon dioxide partial pressure of the subject can be monitored immediately at the beginning of ventilation; furthermore, by determining the target detection site, the carbon dioxide partial pressure of the subject can be monitored by sensors in a timely and effective manner, which provides a reference basis for accurate and timely detection of hyperventilation.

Embodiment 3

Based on the embodiment 2, according to the method, displaying the carbon dioxide partial pressure in real time on the predetermined displayer comprises steps of:

obtaining the carbon dioxide partial pressure of the subject, and ranking the carbon dioxide partial pressure of the subject;

determining target values of the carbon dioxide partial pressure at different time points based on a ranking result, and preprocessing the carbon dioxide partial pressure based on the target values to obtain effective carbon dioxide partial pressure;

extracting data characteristics of the carbon dioxide partial pressure, and determining waveform amplitudes and target points based on the data characteristics;

calling a predetermined visualization component based on the waveform amplitude and the target points, and convert a format of the effective carbon dioxide partial pressure based on the visualization component, so as to obtain graphical data to be displayed; and labeling the graphical data to be displayed in a target graph to obtain a waveform graph of the carbon dioxide partial pressure of the subject, and displaying the waveform graph in real time on the predetermined displayer.

In this embodiment, the target value refers to the carbon dioxide partial pressure of the subject at different time points.

In this embodiment, the preprocessing refers to removing data that is too large or too small for the carbon dioxide partial pressure to ensure that the final carbon dioxide partial pressure is reliable and valid.

In this embodiment, the effective carbon dioxide partial pressure refers to the remaining carbon dioxide partial pressure after removing anomalous data from the carbon dioxide partial pressure.

In this embodiment, the data characteristics refer to the quantity of the effective carbon dioxide partial pressure and the specific value of the effective carbon dioxide partial pressure corresponding to each time point.

In this embodiment, the target points refer to the sampling points for the effective carbon dioxide partial pressure.

In this embodiment, the predetermined visualization component refers to a graphical plug-in for converting the format of the effective carbon dioxide partial pressure.

The beneficial effect of the above technical solution is that by analyzing and processing the carbon dioxide partial pressure of the subject, graphical representation of the carbon dioxide of the subject at different time points can be easily realized, thus improving the accuracy and efficiency of determining whether the subject is hyperventilating or not.

Embodiment 4

Based on the embodiment 1, according to the step 1 of the method, determining whether the subject is experiencing respiratory alkalosis based on the carbon dioxide partial pressure comprises steps of:

obtaining the carbon dioxide partial pressure of the subject, meanwhile obtaining historical training data; determining a standard fluctuation range of the carbon dioxide partial pressure based on the historical training data;

comparing the carbon dioxide partial pressure of the subject with the standard fluctuation range;

if the carbon dioxide partial pressure of the subject is not within the standard fluctuation range, determining whether the carbon dioxide partial pressure of the subject is less than a minimum value of the standard fluctuation range, and if it is less than the minimum value of the standard fluctuation range, determining that the subject satisfies respiratory alkalosis characteristics and providing an alarm alert; and otherwise, determining the carbon dioxide partial pressure of the subject to be normal, and continuously monitoring the carbon dioxide partial pressure of the subject.

In this embodiment, the historical training data refer to fluctuation ranges of the carbon dioxide partial pressure for different subjects when taking ventilator treatment, and the fluctuation range of the carbon dioxide partial pressure corresponds to physical conditions of the different subjects.

In this embodiment, the standard fluctuation range refers to a normal fluctuation range of the carbon dioxide partial pressure allowed in the human body, usually 35-45 mmHg.

In this embodiment, the minimum value refers to a lower limit of the standard fluctuation range.

In this embodiment, satisfying the respiratory alkalosis characteristics means that carbon dioxide partial pressure of the subject is below the standard fluctuation range, i.e., meeting the symptom of low carbon dioxide partial pressure.

The beneficial effect of the above technical solution is that by accurately determining the standard fluctuation range of the carbon dioxide partial pressure based on the historical training data, it facilitates the comparison of the carbon dioxide partial pressure of the subject with the standard fluctuation range, which further facilitates the determination of whether the subject is hyperventilating and experiencing respiratory alkalosis, thereby improving the efficiency and accuracy of respiratory alkalosis determination.

Embodiment 5

Based on the embodiment 4, according to the method, determining that the subject satisfies the respiratory alkalosis characteristics comprises steps of:

collecting a blood sample from the subject based on a predetermined sampling device and performing a PH analysis on the blood sample to obtain a PH value of the subject;

determining acidity or alkalinity of the subject based on the PH value, and determining that the subject has respiratory alkalosis when the subject is alkaline; and otherwise, determining that the subject has an abnormal carbon dioxide partial pressure, and determining a target cause of the abnormal carbon dioxide partial pressure, and optimizing the ventilator device based on the target cause.

In this embodiment, the preset sampling device is set up in advance for blood collection from the subject.

In this embodiment, the blood sample refers to the sample data obtained after sampling the blood of the subject.

In this embodiment, the pH analysis refers to determining the blood pH of the subject by means of a specialized testing agent or appropriate testing instrument.

The beneficial effect of the above technical solution is that the pH value of the subject body is measured in the case of an abnormal carbon dioxide partial pressure, thereby ensuring accurate PH analysis of the subject body, providing reliable and accurate determination of whether the subject has respiratory alkalosis, and facilitating the timely mixing ratio adjustment of the oxygen and the carbon dioxide in the presence of respiratory alkalosis, which can achieve rapid relief of respiratory alkalosis in the subject.

Embodiment 6

Based on the embodiment 1, according to the step 2 of the method, obtaining the vital sign data of the subject when the respiratory alkalosis occurs and determining the degree of the respiratory alkalosis of the subject based on the vital sign data comprise steps of obtaining ID information of a predetermined vital sign measuring device and receiving a vital sign data package collected by the predetermined vital sign measuring device based on the ID information, wherein the predetermined sign measuring device comprises at least one device type;

determining the device type of the predetermined vital sign measuring device based on the ID information, and determining a correspondence between the predetermined vital sign measuring device and a predetermined protocol plug-in based on the device type;

determining a target protocol plug-in for the predetermined vital sign measuring device based on the correspondence, and performing protocol parsing of the vital sign data package based on the target protocol plug-in to obtain initial vital sign data;

extracting attribute information of the initial vital sign data, and determining target cleaning rules for data cleaning of the initial vital sign data based on the attribute information;

cleaning the initial vital sign data based on the target cleaning rules, thereby obtaining target vital sign data of the subject; classifying the target vital sign data based on the attribute information, so as to obtain a target classification result;

determining a waveform profile corresponding to each type of the target vital sign data based on the target classification result, and setting a reference peak point in the waveform profile;

traversing forwards and backwards based on the reference peak points and removing ghost peaks from the waveform profile based on traversal results, so as to obtain a peak time series corresponding to each type of the target vital sign data;

calculating an average spacing of adjacent peak points based on the peak time series, and determining a target change value corresponding to each type of the target vital sign data of the subject based on the average spacing;

performing differentiating calculation on the target change value and a corresponding predetermined threshold to obtain a corresponding target difference value, and comparing the target difference value with the standard fluctuation range corresponding to each type of the target vital sign data; and determining a pH status of the subject based on a comparison result, and determining the degree of the respiratory alkalosis of the subject based on the pH status.

In this embodiment, the predetermined vital sign measuring device is set up in advance for the collection of vital sign data from the subject.

In this embodiment, the ID information is used to mark the data upload address of an interface between the predetermined vital sign measuring device and a statistical backend.

In this embodiment, the vital sign data package refers to a package of vital sign data collected by the predetermined vital sign measuring device, which contains the vital sign data of the subject.

In this embodiment, the device type refers to a function of the predetermined vital sign measuring device, which may be, for example, but is not limited to, an ECG, a blood pressure monitor, etc.

In this embodiment, the predetermined protocol plug-in is used to parse an encapsulated vital sign data package collected by a corresponding device type, which is necessary for the back-end data processing.

In this embodiment, the target protocol plug-in refers to a protocol plug-in used to match the current vital sign measuring device, and is one or more of the predetermined protocol plug-in.

In this embodiment, the attribute information refers to a data type of the vital sign data, a corresponding data volume, etc.

In this embodiment, the initial vital sign data refers to vital sign data obtained by parsing the vital sign data package collected by the predetermined vital sign measuring device, which may contain missing or abnormal vital sign data.

In this embodiment, the target cleaning rule refers to a method for screening or inventorying the vital initial sign data.

In this embodiment, the target vital sign data refer to valid vital sign data obtained by screening the abnormal data from the initial vital sign data under the target cleaning rules.

In this embodiment, the reference peak point is a peak in the waveform profile that is selected as a reference point, so as to traversed forwards or backwards.

In this embodiment, the ghost peak is a peak in the waveform profile that does not represent changes in the vital sign data of the subject.

In this embodiment, the peak time series refers to determining a relationship between each and a corresponding time point.

In this embodiment, the target change value refers to judging a distance between adjacent peaks to determine whether vital sign data change of the subject is regular and whether the distance between adjacent peaks is within a predetermined requirements, which is obtained by comparing the waveform profile with corresponding vital sign data of the subject under normal breathing conditions.

In this embodiment, the predetermined threshold is set in advance to determine whether the target change value is within an acceptable range.

In this embodiment, the target difference value refers to a difference between the target change value and a corresponding predetermined threshold, which measures the degree of difference between current vital sign data of the subject and standard sign data.

In this embodiment, the standard fluctuation range refers to a range within which the vital sign data of subject is allowed to vary from the standard vital sign data.

In this embodiment, obtaining the target vital sign data of the subject comprises steps of:

obtaining the target vital sign data of the subject, and determining arterial oxygen partial pressure and venous oxygen partial pressure of the subject based on the target vital sign data;

calculating arterial oxygen saturation of the subject based on the arterial oxygen partial pressure and the venous oxygen partial pressure, and calculating cerebral oxygen utilization of the subject based on the arterial oxygen saturation, which comprise specific steps of:

calculating the arterial oxygen saturation of the subject according to the following equation:

$$\alpha = \frac{v}{V} * \frac{\beta - a * (\delta - \tau)}{\mu * b} - \varphi;$$

wherein α indicates the arterial oxygen saturation of the subject; v indicates a blood flow velocity corresponding to a peak of an arterial blood flow systole of the subject; V indicates a blood flow velocity corresponding to an end of the arterial blood flow systole of the subject; F indicates a difference between arterial and venous oxygen levels of the subject; a indicates a constant with a range of (0.003, 0.01); δ indicates the arterial oxygen partial pressure of the subject; τ indicates the venous oxygen partial pressure of the subject; μ indicates a hemoglobin content of the subject; b indicates a constant with a range of (1.25, 1.55); φ indicates a mixed venous oxygen saturation of the subject; and calculating the cerebral oxygen utilization of the subject according to the following equation;

$$\eta = (1 - \omega) * \frac{\alpha - \varphi}{\alpha} * 100\%;$$

wherein η represents the cerebral oxygen utilization of the subject with a range of (0, 1); ω represents an error factor with a range of (0.02, 0.05); α represents the arterial oxygen saturation of the subject; and φ represents the mixed venous oxygen saturation of the subject; and determining a gas supply volume to the subject based on the cerebral oxygen utilization, and mixing the oxygen with the carbon dioxide based on the gas supply volume and delivering the mixed gas to the subject.

The cerebral oxygen utilization refers to an extent to which the subject utilizes the inhaled oxygen.

The beneficial effect of the above technical solution is that the vital sign data of the subject is measured by the predetermined vital sign measuring device, and is analyzed to obtain the change of the vital sign data of the subject, ensuring that the collected vital sign data of the subject is accurate and reliable. Meanwhile, based on the degree of difference between the vital sign data of the subject and the standard vital sign data, the current degree of the respiratory alkalosis of the subject can be accurately determined, which facilitates accurate adjustment of the gas mixing ratio of the subject to ensure effective resolution of the respiratory alkalosis of the subject.

Embodiment 7

Based on the embodiment 6, according to the method, determining a pH status of the subject based on a comparison result, and determining the degree of the respiratory alkalosis of the subject based on the pH status comprises steps of:

obtaining the pH status of the subject, and determining bicarbonate ion concentration in the subject based on the pH status;

determining a concentration difference between the bicarbonate ion concentration and a standard bicarbonate ion concentration threshold, and comparing the concentration difference with a first difference threshold and a second difference threshold, respectively;

if the concentration difference is less than the first difference threshold, determining that the subject has mild respiratory alkalosis and sending a first alarm alert; and if the concentration difference is no less than the first difference threshold and less than the second difference threshold, determining that the subject has moderate respiratory alkalosis and sending a second alarm alert; and otherwise, determining that the subject has severe respiratory alkalosis and sending a third alarm alert.

In this embodiment, the bicarbonate ion concentration refers to a concentration obtained after ion reaction in the subject during using the ventilator device, wherein a higher concentration indicates higher respiratory alkalosis in the subject.

In this embodiment, the standard bicarbonate ion concentration threshold is set in advance to indicate a value of a bicarbonate ion concentration allowed to be received in the body.

In this embodiment, the first difference threshold and the second difference threshold are set in advance to measure an extent to which the bicarbonate ion concentration in the subject exceeds the standard bicarbonate ion concentration threshold.

In this embodiment, the first alarm alert can be, for example, a sound alarm.

In this embodiment, the second alarm alert can be, for example, a light alarm.

In this embodiment, the third alarm alert can be, for example, a combination of sound and light alarms.

The beneficial effect of the above technical solution is that by analyzing the degree of the respiratory alkalosis of the subject, alarm operation corresponding to each degree of the respiratory alkalosis of the subject can be performed, so that the gas mixing ratio can be adjusted in time according to the alarm operation, thus ensuring the safety of the subject.

Embodiment 8

Based on the embodiment 1, according to the step 3 of the method, adjusting the mixing ratio of the oxygen and the carbon dioxide based on the degree of the respiratory alkalosis, then re-supplying the subject, and monitoring the respiratory status of the subject in real time comprise steps of:

obtaining the degree of the respiratory alkalosis of the subject, meanwhile sampling a gas mixture currently received by the subject and analyzing the gas mixture based on a sampling result, so as to obtain an initial mixing ratio of the oxygen and the carbon dioxide in the gas mixture;

extracting a target characteristic of the degree of the respiratory alkalosis in the subject and determining a target carbon dioxide ratio adjustment range for mitigating the degree of the respiratory alkalosis in the subject based on the target characteristic, wherein the target carbon dioxide ratio adjustment range is 1%-6%;

determining an initial adjustment parameter for a carbon dioxide mixing ratio in the initial mixing ratio of the oxygen and the carbon dioxide based on the target carbon dioxide ratio adjustment range, and adjusting the initial mixing ratio of the oxygen and the carbon dioxide based on the initial adjustment parameter to obtain a baseline mixing ratio;

determining a gas pressure of the oxygen and the carbon dioxide through the ventilator device based on the baseline mixing ratio, and regulating a pressure balance of the oxygen and the carbon dioxide based on the gas pressure;

mixing the oxygen with the carbon dioxide based on a pressure balance regulation result to obtain a baseline gas mixture, and delivering the baseline gas mixture to the subject based on the ventilator device;

monitoring respiration data of the subject in real time based on a delivery result, and adjusting a carbon dioxide ratio in the baseline gas mixture in a gradient form based on the respiration data; and determining a delivering period of the gas mixture of each gradient based on gradient adjustment results, and delivering the gas mixture of each gradient to the subject based on the delivering period until the respiratory data of the subject returns to normal, thus completing mixture adjustment of the oxygen and the carbon dioxide.

In this embodiment, the initial mixing ratio refers to a current mixing ratio of the oxygen to the carbon dioxide received by the subject.

In this embodiment, the target characteristic refers to a change in the vital sign data of the subject, which may be, for example, the difference between the vital sign data and the standard sign data.

In this example, the target carbon dioxide ratio adjustment range refers to an extent to which the ratio of the carbon dioxide in the initial mixture needs to be adjusted, which is 1%-6%.

In this embodiment, the initial adjustment parameter refers to an extent of an initial adjustment, wherein the ratio of the carbon dioxide scaling is modified by 1%-6% in a gradient form.

In this embodiment, the baseline mixing ratio refers to the gas mixture that is re-supplied to the subject after adjusting the ratio of the carbon dioxide in the initial mixing ratio, wherein the ratio of the carbon dioxide is continuously adjusted according to the baseline mixing ratio until the respiratory alkalosis of the subject is resolved.

In this embodiment, the pressure balance regulation means optimizing the pressure of the two gases according to the input pressure of the oxygen and the carbon dioxide to ensure that the two gases can be mixed.

In this embodiment, the baseline gas mixture refers to the mixture obtained by mixing the oxygen with the carbon dioxide and sine according to the base mixture ratio.

In this embodiment, the respiratory data refers to the subject heart rate, pulse rate, etc.

The beneficial effect of the above technical solution is that the ratio of the carbon dioxide is accurately adjusted according to the degree of the respiratory alkalosis of the subject, and the pressure balance of the oxygen and the carbon dioxide is regulated after the adjustment, so that the gas mixture can be effectively transferred to the subject. This improves the effectiveness of treating the respiratory alkalosis and also ensures the safety of the subject.

Embodiment 9

Embodiment 8, according to the method, monitoring respiration data of the subject in real time based on the delivery result comprises steps of:

obtaining a real-time monitoring result of the respiratory data of the subject, and determining a heartbeat waveform profile corresponding to the respiratory data of the subject based on the real-time monitoring result;

determining whether the subject has respiratory abnormalities based on the heartbeat waveform profile;

determining a target cause of the respiratory abnormalities of the subject if the respiratory abnormalities exist, and adjusting the respiratory abnormalities of the subject based on the target cause; and otherwise, monitoring the respiratory data of the subject in real time until the respiratory data of the subject returns to normal, then switching an operating mode of the ventilator device, wherein the operating mode comprises mixing oxygen and carbon dioxide and mixing oxygen and air.

In this embodiment, the heartbeat waveform profile refers to an ECG waveform of the subject.

In this embodiment, determining whether the subject has respiratory abnormalities based on the heartbeat waveform profile means comparing the heartbeat waveform profile of the subject with the heartbeat waveform profile under normal conditions to determine whether the subject has the respiratory abnormality.

In this embodiment, the target cause refers to factors that cause abnormal breathing in the subject, such as, but not limited to, abnormalities in personal physical parameters and abnormalities in the ventilator device.

In this embodiment, the operating modes refer to two modes of air supply that the ventilator device can provide, which are mixing oxygen and carbon dioxide, and mixing oxygen and air.

The beneficial effect of the above technical solution is that by adjusting the mixing ratio of the carbon dioxide in the gas mixture, the respiratory condition of the subject is monitored in real time, and the cause of abnormality can be solved in time when the respiratory condition of subject is abnormal, thus ensuring that the respiratory alkalosis of the subject can be solved effectively, and the efficiency and safety of the treatment are improved.

Embodiment 10

Figure 2:
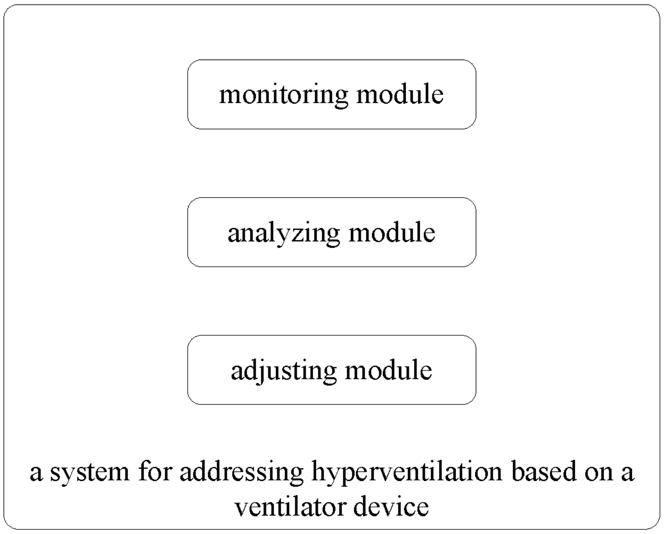
FIG. 2 is a structural view of a system for addressing hyperventilation based on a ventilator device according to an embodiment of the present invention.

This embodiment provides a system for addressing hyperventilation based on a ventilator device is provided, as shown in FIG. 2, comprising:

- a monitoring module for obtaining a carbon dioxide partial pressure of a subject, and determining whether the subject is experiencing respiratory alkalosis based on the carbon dioxide partial pressure;
- an analyzing module for obtaining vital sign data of the subject when the respiratory alkalosis occurs and determining a degree of the respiratory alkalosis of the subject based on the vital sign data; and
- an adjusting module for adjusting a mixing ratio of oxygen and carbon dioxide based on the degree of the respiratory alkalosis, then re-supplying the subject; and monitoring a respiratory status of the subject in real time.

Figure 3:
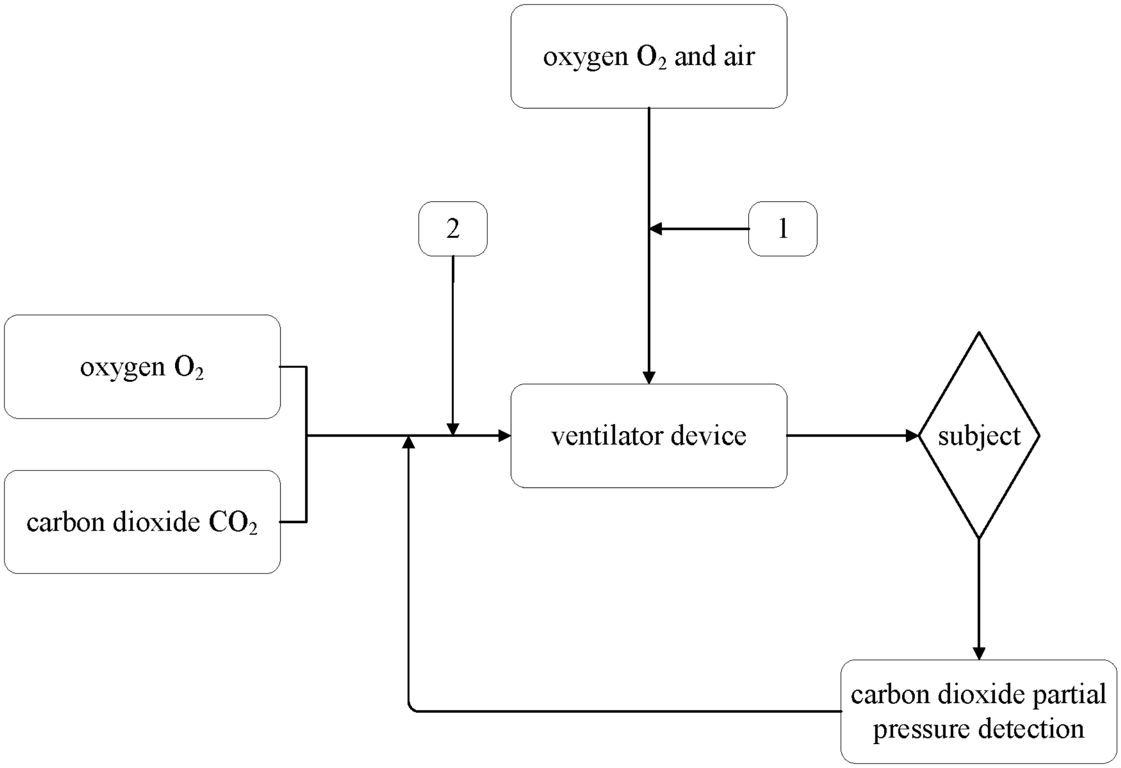
FIG. 3 illustrates supply principles of the ventilator device on which the system for addressing the hyperventilation is based according to the embodiment of the present invention.

In this embodiment, working principles of the ventilator device are shown in FIG. 3, wherein 1 and 2 are the two modes of air supply of the ventilator device.

The beneficial effect of the above technical solution is that by monitoring the carbon dioxide partial pressure of the subject, it can quickly and accurately determine whether the subject is suffering from the respiratory alkalosis, and by adjusting the mixing ratio of the oxygen and the carbon dioxide, the system can effectively relieve the respiratory alkalosis of the subject and improve the efficiency and safety of solving the respiratory alkalosis caused by hyperventilation.

It is clear that a person skilled in the art may make various modifications and variations of the present invention without departing from the spirit and scope thereof. Thus, if such modifications and variations are within the scope of the claims of the present invention and their technical equivalents, the present invention is also intended to include such modifications and variations.

What is claimed is:

1. A method for addressing hyperventilation based on a ventilator device, comprising:

- obtaining a carbon dioxide partial pressure of a subject, and determining whether the subject is experiencing respiratory alkalosis based on the carbon dioxide partial pressure;
- obtaining identity information of a predetermined vital sign measuring device and receiving a vital sign data package collected by the predetermined vital sign measuring device based on the identity information, wherein the predetermined vital sign measuring device comprises at least one device type;
- determining the device type of the predetermined vital sign measuring device based on the identity information, and determining a correspondence between the predetermined vital sign measuring device and a predetermined protocol plug-in based on the device type;
- determining a target protocol plug-in for the predetermined vital sign measuring device based on the correspondence, and performing protocol parsing of the vital sign data package based on the target protocol plug-in to obtain initial vital sign data;
- extracting attribute information of the initial vital sign data, and determining target cleaning rules for data cleaning of the initial vital sign data based on the attribute information;
- cleaning the initial vital sign data based on the target cleaning rules, thereby obtaining target vital sign data of the subject; classifying the target vital sign data based on the attribute information, so as to obtain a target classification result;
- determining a waveform profile corresponding to each type of the target vital sign data based on the target classification result, and setting a reference peak point in the waveform profile;
- traversing forwards and backwards based on the reference peak points and removing ghost peaks from the waveform profile based on traversal results, so as to obtain a peak time series corresponding to each type of the target vital sign data;
- calculating an average spacing of adjacent peak points based on the peak time series, and determining a target change value corresponding to each type of the target vital sign data of the subject based on the average spacing;
- performing differentiating calculation on the target change value and a corresponding predetermined threshold to obtain a corresponding target difference value, and comparing the target difference value with a standard fluctuation range corresponding to each type of the target vital sign data; and
- determining a pH status of the subject based on a comparison result between the target difference value and a standard fluctuation range, and determining a degree of the respiratory alkalosis of the subject based on the pH status; and
- adjusting a mixing ratio of oxygen and carbon dioxide based on the degree of the respiratory alkalosis, then re-supplying the subject, and monitoring a respiratory status of the subject in real time;
- wherein adjusting the mixing ratio of the oxygen and the carbon dioxide based on the degree of the respiratory alkalosis, then re-supplying the subject, and monitoring the respiratory status of the subject in real time comprise steps of:
- obtaining the degree of the respiratory alkalosis of the subject, meanwhile sampling a gas mixture currently received by the subject and analyzing the gas mixture based on a sampling result, so as to obtain an initial mixing ratio of the oxygen and the carbon dioxide in the gas mixture;
- extracting a target characteristic of the degree of the respiratory alkalosis in the subject and determining a target carbon dioxide ratio adjustment range for mitigating the degree of the respiratory alkalosis in the subject based on the target characteristic, wherein the target carbon dioxide ratio adjustment range is 1%-6%;
- determining an initial adjustment parameter for a carbon dioxide mixing ratio in the initial mixing ratio of the oxygen and the carbon dioxide based on the target carbon dioxide ratio adjustment range, and adjusting the initial mixing ratio of the oxygen and the carbon dioxide based on the initial adjustment parameter to obtain a baseline mixing ratio;
- determining a gas pressure of the oxygen and the carbon dioxide through the ventilator device based on the baseline mixing ratio, and regulating a pressure balance of the oxygen and the carbon dioxide based on the gas pressure;

mixing the oxygen with the carbon dioxide based on the regulated pressure balance to obtain a baseline gas mixture, and delivering the baseline gas mixture to the subject based on the ventilator device;

monitoring respiration data of the subject in real time based on a delivery result, and adjusting a carbon dioxide ratio in the baseline gas mixture in a gradient form based on the respiration data; and determining a delivering period of the gas mixture of each gradient based on gradient adjustment results, and delivering the gas mixture of each gradient to the subject based on the delivering period until the respiratory data of the subject returns to normal, thus completing mixture adjustment of the oxygen and the carbon dioxide.

* * * * *